(12) United States Patent
Ponomarev et al.

(10) Patent No.: US 8,779,548 B2
(45) Date of Patent: Jul. 15, 2014

(54) INTEGRATED CIRCUIT INCLUDING A POROUS MATERIAL FOR RETAINING A LIQUID AND MANUFACTURING METHOD THEREOF

(75) Inventors: Youri Victorovitch Ponomarev, Leuven (BE); Aurelie Humbert, Brussels (BE); Roel Daamen, Herkenbosch (NL)

(73) Assignee: NXP, B.V., Eindhoven (NL)

( * ) Notice: Subject to any disclaimer, the term of this patent is extended or adjusted under 35 U.S.C. 154(b) by 296 days.

(21) Appl. No.: 12/843,809

(22) Filed: Jul. 26, 2010

(65) Prior Publication Data
US 2011/0018097 A1 Jan. 27, 2011

(30) Foreign Application Priority Data
Jul. 27, 2009 (EP) ..................... 09166518

(51) Int. Cl.
*H01L 23/29* (2006.01)
*H01L 23/31* (2006.01)
(52) U.S. Cl.
CPC ..... *H01L 23/3107* (2013.01); *H01L 2924/0002* (2013.01); *H01L 2924/3011* (2013.01); *H01L 23/291* (2013.01); *H01L 2924/19041* (2013.01)
USPC .............. 257/529; 257/E29.343; 257/E21.08; 257/532; 438/396
(58) Field of Classification Search
USPC .............. 257/532, E29.343, E21.08; 438/369
See application file for complete search history.

(56) References Cited

U.S. PATENT DOCUMENTS

| | | | |
|---|---|---|---|
| 4,057,823 A | 11/1977 | Burkhardt et al. | |
| 5,546,802 A | 8/1996 | Yoshimura et al. | |
| 6,603,319 B1 | 8/2003 | Kasahara et al. | |
| 2004/0008471 A1 | 1/2004 | Davis et al. | |
| 2005/0194649 A1 | 9/2005 | Oki | |
| 2008/0191716 A1 | 8/2008 | Chen et al. | |
| 2009/0141767 A1* | 6/2009 | Cummins | 374/142 |
| 2011/0018097 A1* | 1/2011 | Ponomarev et al. | 257/532 |

FOREIGN PATENT DOCUMENTS

| | | |
|---|---|---|
| JP | 7094567 A | 4/1995 |
| WO | 2005095936 A1 | 10/2005 |
| WO | 2007057794 A1 | 5/2007 |

OTHER PUBLICATIONS

J.J. Bao et al., "Mechanistic Study of Plasma Damage and CH4 Recovery of Low k Dielectric Surface," Proc. of the IEEE Intl. Interconnect Technology Conference, 2007, pp. 147-149.
M.J. Park et al., "Increased Water Retention in Polymer Electrolyte Membranes at Elevated Temperatures Assisted by Capillary Condensation," Nano Letters, 2007, vol. 11 pp. 3547-3552.
Graham et al., "Formation of a porous alumina electrode as a low-cost CMOS neuronal interface," Sensors and Actuators B, 138, 2009, pp. 296-303.
Extended European Search Report, European Patent Office, Dec. 30, 2009.

* cited by examiner

*Primary Examiner* — Tom Thomas
*Assistant Examiner* — Elias M Ullah

(57) ABSTRACT

Disclosed is an integrated circuit (IC) comprising a substrate (10) including a plurality of circuit elements and a metallization stack (20) covering said substrate for providing interconnections between the circuit elements, wherein the top metallization layer of said stack carries a plurality of metal portions (30) embedded in an exposed porous material (40) for retaining a liquid, said porous material laterally separating said plurality of metal portions. An electronic device comprising such an IC and a method of manufacturing such an IC are also disclosed.

20 Claims, 2 Drawing Sheets

INTEGRATED CIRCUIT INCLUDING A POROUS MATERIAL FOR RETAINING A LIQUID AND MANUFACTURING METHOD THEREOF

FIELD OF THE INVENTION

The present invention relates to an integrated circuit (IC) comprising a substrate including a plurality of circuit elements and a metallization stack covering said substrate for providing interconnections between the circuit elements.

The present invention further relates to a method of manufacturing such an IC.

BACKGROUND OF THE INVENTION

Nowadays, integrated circuits (ICs) routinely comprise patterned metallization layers for interconnecting circuit elements, e.g. transistor terminals in the substrate or to provide external access, e.g. bond pads, to the circuit elements that are embedded in the semiconductor device. Typically, the metallization layers are formed by stacking and patterning dielectric layers and metal layers to obtain the required interconnections. The dielectric and metal layers themselves may contain sub-layers. The dielectric layers typically comprise vias to conductively connect metal portions in the different metal layers with each other.

Rigorous testing of the ICs, e.g. when they are still part of a wafer, takes place to ensure that the IC operates correctly, e.g. is free of manufacturing defects. This is important because the IC may be integrated into an electronic device, where the failure of the IC in the electronic device would most likely cause the electronic device to exhibit faulty behavior. For this reason, significant efforts are made to ensure that defective ICs are removed from a batch of manufactured ICs to avoid field returns of electronic devices containing such ICs as much as possible. Field returns inconvenience the customer, and can lead to a loss of business because of the customer losing faith in the product. Nevertheless, it is very difficult to capture all defective ICs such that it cannot be avoided that some defective ICs enter the market, e.g. inside an electronic device. On the other hand, a returned faulty electronic device may have entered the market functioning correctly, where it is possible that the fault has developed through misuse of the semiconductor device, e.g. by the customer accidentally submerging the device in water. Obviously, in such a case, the manufacturer cannot be held responsible for the failure of the device.

It is difficult to establish why a semiconductor device returned from the field has failed. Re-engineering the device to determine the cause of failure is not always successful and is cost-prohibitive for single devices. U.S. Pat. No. 4,057,823 discloses a structure for a relative humidity monitor which can be built into an integrated circuit chip. A small area on a silicon chip is made porous by anodic etching. This region is then oxidized and a metal counter electrode is deposited over part of the porous area. Due to the relatively large surface area in the dielectric under the counter electrode and the openness of the structure, ambient moisture can quickly diffuse into the dielectric under the electrode and adsorb onto the silicon dioxide surface, such that changes in ambient humidity will be reflected by measurable changes in capacitance or conductance of the device.

A drawback of such a moisture sensor is that in other to determine if an electronic device returned from the field has been subjected to excess moisture, the sensor must be continuously monitored during the operational life of the electronic device and its measurements, or at least measurements exceeding a predefined threshold, stored for future read-out. This is an impractical solution.

SUMMARY OF THE INVENTION

The present invention seeks to provide an IC in which its exposure to water does not have to be detected during the actual exposure.

The present invention further seeks to provide a method of manufacturing such an IC.

In accordance with a first aspect of the present invention, there is provided an integrated circuit comprising a substrate including a plurality of circuit elements and a metallization stack covering said substrate for providing interconnections between the circuit elements, wherein the top metallization layer of said stack carries a plurality of metal portions embedded in an exposed porous material for retaining a liquid, said porous material laterally separating said plurality of metal portions.

The present invention has been based on the realization that porous materials capable of retaining water after the material has been exposed to the water can be advantageously used to store water in a sensor area upon exposure of the area to the water. The sensor is formed by two or more metal portions on top of the metallization stack of the IC, with the porous water-retaining material separating, i.e. electrically insulating the metal portions from each other. Consequently, the detection of the exposure can be delayed, e.g. upon return of the IC to its manufacturer, such that permanent monitoring of the sensor to detect the immersion of the IC in water is unnecessary. Alternatively, the immersion sensor can be interrogated for warranty claim validation purposes for (expensive) electronic devices by the vendor of the electronic devices, e.g. by means of a suitable wireless interface to the sensor, such as a RFID/NFC interface such that the IC of the present invention does not have to be returned to the IC manufacturer for this interrogation.

It is pointed out that the anodically etched oxide of the relative humidity monitor disclosed in U.S. Pat. No. 4,057,823 is not a water-retaining material. In the context of the present invention, a water-retaining material is a material showing hysteresis towards the amount of water in the environment to which the material is exposed. In other words, suitable materials for use as the porous material for retaining a liquid in the IC of the present invention are materials from which water cannot be (easily) removed under the normal operating conditions of the IC or the electronic device into which the IC has been integrated upon removal of the water from the sensor surroundings, e.g. by drying the IC or the electronic device. Such materials are known per se. For instance, several examples exist of porous dielectric materials having a low intrinsic dielectric constant, so-called low-k dielectrics, in which a pore diameter in the nanometer domain causes water to be retained in the material.

For instance, it is known from J. J. Bao et al. in Proc. of the IEEE Intl. Interconnect Technology Conference, 2007, pages 147-149 that carbon-doped silicon oxide after treatment with a plasma such as an O2, N2 or Ar plasma tends to retain water, which proved difficult to remove even at elevated temperatures. Another dielectric material known to retain water is SiLK, which is a spin-on dielectric material manufactured by The Dow Chemical Company, having pore sizes in the nm domain. Nanoclustered silica (NCS)-based materials are another example of a porous material capable of retaining water. Other examples will be apparent to the skilled person, such as water retaining polymer electrolyte membranes reported in Nano Letters, 2007, Vol. 11 pages 3547-3552 by M. J. Park et al.

It should be understood that for the above examples of suitable water-retaining materials, these water-retaining properties are traditionally considered a disadvantage or nuisance because it complicates the manufacturing process of ICs comprising such materials due to the fact that the moisture levels in the environment in which the ICs are manufactured must be kept extremely low to avoid water retention in these materials because the removal of such retained water is extremely difficult, with temperatures in excess of 400° C. sometimes even being insufficient to remove the water.

As will be readily understood by the skilled person, such water retention affects (increases) the dielectric constant of the materials, which can be highly undesirable if such a material is to act as an insulator within the IC. However, the present invention is based on the realization that this change of the dielectric constant can be utilized to detect the exposure (immersion) of the IC in water.

It is not necessary for the water-retaining porous material to cover the complete metallization stack. In an embodiment, the porous material is a patterned layer covering the plurality of metal portions.

In order to access the water exposure sensor, a selection of the circuit elements may be connected to the plurality of metal portions through the metallization stack, said selection forming a circuit for measuring the impedance between said metal portions. The impedance may be measured in the form as a capacitance measurement. Alternatively, ion conductivity between two metal portions, which is correlated to the amount of water retained in the porous material between the metal portions may be measured. The circuit may be accessible in any suitable manner, e.g. through dedicated pins or through a test access port used for testing the IC, such as a boundary scan-compliant (IEEE 1149.1) test access port or a system-on-chip-compliant (IEEE 1500) test access port. This has the advantage that the pin count of the IC can be reduced because no dedicated access pins are necessary.

Alternatively, the circuit for measuring the impedance between the metal portions may be located off-chip, such that in an embodiment the IC further comprises a plurality of terminals conductively coupled to respective metal portions of said plurality of metal portions for measuring the impedance between said metal portions. This reduces the circuitry overhead of the IC at the cost of additional pins for providing external access to the water exposure sensor of the present invention.

The porous material used in the IC of the present invention as a water-retaining material does not need to have nanometer scale pores. In an alternative embodiment, the porous material may simply serve as a water reservoir, with the water retention properties being provided by a capping layer covering the porous material, said capping layer comprising a plurality of capillaries for exposing the porous material. An example of a suitable capping layer material is anodically oxidized aluminum, which is a nanoporous material comprising the necessary capillary structure, as is known from Sensors and Actuators B, 138, 2009, pages 296-303 by A. H. D. Graham et al.

The IC of the present invention may be advantageously integrated into an electronic device to allow the detection of the exposure of the electronic device to water. In the context of the present application, the term electronic device is intended to cover any device or apparatus that can receive the IC of the present invention, including consumer electronic devices such as mobile communication devices, (laptop) computers as well as medical devices, automotive devices and so on.

According to another aspect of the present invention, there is provided a method of manufacturing an integrated circuit, comprising providing a substrate; forming a plurality of circuit elements on said substrate; forming a metallization stack covering said substrate for providing interconnections between the circuit elements, forming, on top of said metallization stack, a plurality of metal portions; and embedding said plurality of metal portions in an exposed porous material for retaining a liquid, said porous material laterally separating said plurality of metal portions.

This allows for the manufacturing of the IC of the present invention in existing semiconductor technologies such as CMOS technology. The method may further comprise patterning said porous material to provide access to parts of the metallization stack not carrying a water exposure sensor. The method may further comprise depositing a capping layer over said porous material, said capping layer comprising a plurality of capillaries for exposing the porous material such that the porous material itself does not need to have water retaining properties.

BRIEF DESCRIPTION OF THE EMBODIMENTS

Embodiments of the invention are described in more detail and by way of non-limiting examples with reference to the accompanying drawings, wherein FIG. 1 depicts an embodiment of the IC of the present invention;

DETAILED DESCRIPTION OF THE DRAWINGS

Figure 1:
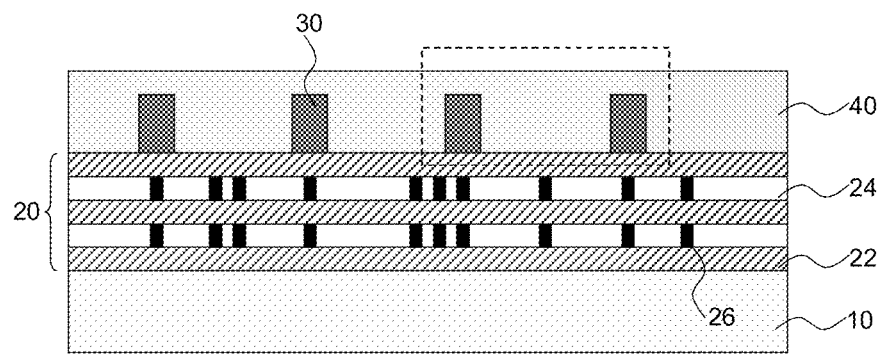

It should be understood that the Figures are merely schematic and are not drawn to scale. It should also be understood that the same reference numerals are used throughout the Figures to indicate the same or similar parts.

FIG. 1 schematically depicts an IC in accordance with an embodiment of the present invention. The IC of the present invention may be provided using any suitable manufacturing technology, such as CMOS, silicon-on-insulator and SiGe technologies. The IC comprises a substrate 10, e.g. a Si substrate, a SiGe substrate and so on, which typically comprises a plurality of circuit elements such as transistors, diodes, and so on, combinations of which from circuits. These may be analog or digital circuits. It should be understood that the present invention is not limited to specific types of ICs. The present invention may be included in any suitable IC, including digital ICs, analog ICs and mixed signal ICs.

The interconnections between the circuit elements in the substrate 10 to define the circuits are typically provided by a metallization stack 20, which by way of non limiting example may comprise a plurality of patterned metal layers 22 separated by dielectric layers 24. Any suitable number of metal layers 12 and dielectric layers 14 may be present. Metal portions in different metal layers 22 may be conductively interconnected by one or more vias 26 formed in a dielectric layer 24 in between the respective portions of the metal layers 22. Any suitable material may be used to form the metallization stack 20, such as Ti, TiN, Al, Cu and combinations thereof to define the metal layers 22 and silicon oxide, silicon nitride, low-k dielectrics and other dielectric materials as well as combinations thereof to form the dielectric layers 24. Although in FIG. 1 these layers are depicted as single layers, it should be understood that these layers themselves may comprise a stack of layers, as is common design practice in contemporary semiconductor technologies such as sub-micron CMOS technologies.

In accordance with the present invention, the top metal layer 22 of the metallization stack 20 comprises metal portions 30, which may be formed in the top metal layer 22 or may be deposited on top of the top metal layer 22. Both embodiments are feasible. The metal portions 30 are conductively coupled to the metallization stack 20, for reasons that will be explained in more detail later. Any suitable metal may be used for the metal portions 30. Preferably, the metal used is the same metal as used in the metallization stack 20 such that the metal portions 30 may be realized using the same processing steps used for the formation of the metal layers 22 such that the complexity of the IC manufacturing process is not significantly increased, i.e. the manufacturing cost of the IC is not significantly increased. Since it is well-known to the skilled person how to form such metal portions 30, this will not be further explained for reasons of brevity only.

The metal portions 30 are embedded in, i.e. covered by, a liquid retention material 40. The liquid preferably is water. The liquid retention material 40 exhibits water retention hysteresis behavior, which means that upon immersion of the material 40 in water, subsequent exposure of the material to a low humidity environment does not lead to the release of the water from the liquid retention material 40. In addition, the liquid retention material 40 should have a weak response to changes in relative humidity, i.e. should not exhibit sensitivity to water present in the atmosphere in a vapor or gas phase. Such materials are known per se. For instance, porous materials having nanometer or micron pore sizes are known that show the desired behavior. Examples of such a material include nanoclustered silicates, such as the material disclosed by J. J. Bao et al. in Proc. of the IEEE Intl. Interconnect Technology Conference, 2007, pages 147-149, which was demonstrated to retain moisture whilst the system comprising the material was heated to 250° C. for 1 hour.

Suitable porous low-k dielectric materials are especially promising because they may be deposited using conventional processing techniques, thus not requiring significant modification of the manufacturing process. In the context of the present invention, a low-k dielectric material is a material having a dielectric constant of less than five, and preferably less than three. SiLK™, a low-k dielectric produced by The Dow Chemical Company, is another non-limiting example of a suitable liquid retention material 40. Polymer materials, and in particular polymer electrolyte membrane materials such as polystyrenesulfonate-block-polymethylbutylene, also show the required water retention behavior. Other examples of suitable polymers will be apparent to the skilled person.

In the context of the present invention, a porous material may be any material that comprises interconnected nanometer sized pores, i.e. materials intrinsically comprising such pores or materials in which such pores have been artificially created.

The principle of the liquid immersion sensor embedded in the IC of the present invention will be explained in more detail with the aid of FIG. 2, in which the portion of the IC of FIG. 1 identified by the dashed box in FIG. 1 has been depicted. Neighboring metal portions 30 are separated by a dielectric medium forming part of the water retention layer 40. The metal portions 30 are connected to a measurement circuit 50 through the metallization stack 20 in case of the measurement circuit 50 being formed by a selection of circuit elements on the substrate 10, or through bond pads (not shown) through the liquid retention layer 40 in case of the measurement circuit 50 being external to the IC. An impedance measurement across the portion of the liquid retention layer 40 in between the neighboring metal portions 30 can be performed to determine if the IC has been exposed to excessive humidity levels, e.g. has been immersed in water.

Figure 2:
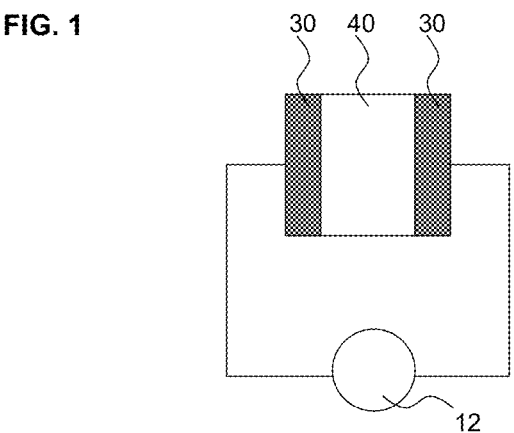
FIG. 2 depicts an aspect of an embodiment of the IC of the present invention.

In FIG. 2, an arrangement is shown in which the liquid immersion sensor comprises a capacitor, with the metal portions 30 forming the plates of the capacitor and the portion of the liquid retention layer 40 forming the dielectric separating the capacitor plates. Since the capacitance C of the capacitor is defined as $C = \in \cdot A/d$, with $\in$ being the electric permittivity (or dielectric constant) of the water retention material 40, A being the area of the capacitor plates (i.e. the metal portions 30) and being the distance between the capacitor plates (i.e. the thickness of the portion of the of the liquid retention layer 40 in between the metal portions 30), any change in the permittivity of the water retention material 40 causes a corresponding change in the capacitance of the aforementioned capacitor, thus enabling the detection of the exposure of the water retention material 40 to excess moisture. For instance, a material 40 is chosen in which the dielectric constant is:

less than three when the material has not been exposed to moisture;

less than five when the material has not been exposed to moisture levels of less than 99% relative humidity; and over twenty if the pores of the material have been filled with water following the exposure of the electronic device comprising the IC with the water exposure sensor to excess water, e.g. following the immersion of the electronic device in water.

It should be understood that any liquid retention material 40 may be chosen that exhibits a sufficiently large variation in dielectric constant upon exposure to different moisture levels. In the above example, capacitance was used as a parameter for detecting the exposure to excess moisture levels. It should however be understood that capacitance was chosen by way of non-limiting example and that other parameters that are dependent of the permittivity of the water retention material 40, such as ion conductivity may instead be utilized.

The read-out of the liquid immersion sensor may be realized in any suitable manner. For instance, the capacitance increase of a capacitor-based liquid immersion sensor may be detected by using a differential measurement in which its capacitance is compared with the capacitance of a reference capacitor that has the same initial capacitance as the liquid immersion sensor and which is not sensitive to variations in the moisture levels to which the IC is exposed, e.g. by using a moisture-insensitive dielectric material for the reference capacitor or by placing the reference capacitor in the lower metal layers 22 of the metallization stack 20.

Figure 3:
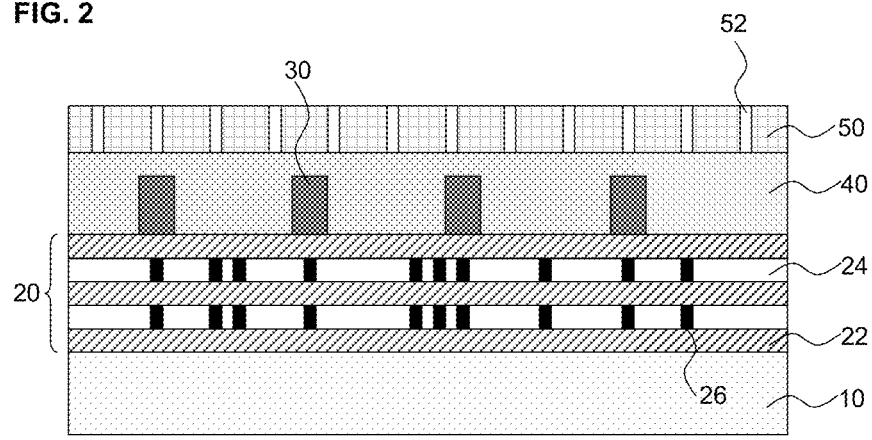
FIG. 3 depicts another embodiment of the IC of the present invention.

It is not necessary that the liquid retention material 40 is the top layer of the IC, i.e. is directly exposed to the environment of the IC or electronic device comprising the IC. FIG. 3 shows an alternative embodiment in which a capping layer 50 comprising capillaries 52 caps the liquid retention material 40. Such a capping layer 50 may be used to protect the liquid retention material 40, or may be used as a barrier layer for substances other than water to add selectivity to the sensor concept of the present invention. Alternatively, the barrier layer 50 may provide water retention characteristics to a porous layer 40 not exhibiting such hysteresis, e.g. a spin-on zeolite material having a relatively large pore size. Suitable examples of such a capping layer 50 comprise porous aluminum, which may be formed by anodically etching the aluminum as for instance disclosed in the aforementioned paper by A. H. D. Graham et al.

Figure 4:
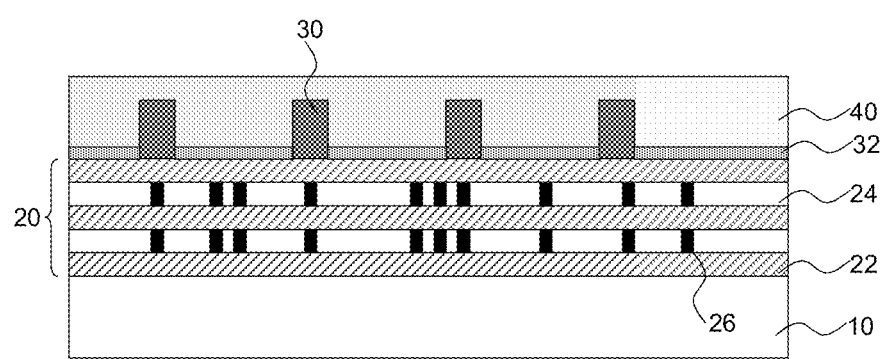
FIG. 4 depicts yet another embodiment of the IC of the present invention.

If required, the IC may further comprise a liquid barrier layer for protecting the metallization stack 20 and the circuit elements in the substrate 10 from liquid exposure, and in particular from water exposure. FIG. 4 shows an embodiment in which a liquid barrier layer 32 is present in between the metal portions 30. Such a barrier layer may be formed over the metallization stack 20 and subsequently patterned to form the holes in which the metal portions 30 are formed, after which the metal portions 30 may be formed in these patterned holes. In an alternative embodiment (not shown), the liquid barrier layer 32 extends over the metallization stack 20 such that the metal portions 30 are formed on top of the water barrier layer 32. In this embodiment, the water barrier layer 32 should have a high enough dielectric constant in case the measurement circuit 50 is formed in the substrate 10 to facilitate a conductive communication between the metallization stack 20 and the metal portions 30 and to prevent interference with a capacitance measurement of the liquid immersion sensor formed by the metal portions 30 and the portion of the liquid retention layer 40 separating these metal portions. Non-limiting examples of suitable materials for the water barrier layer 32 in this embodiment include silicon oxide, silicon nitride, silicon carbide and tantalum pentoxide materials.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An apparatus comprising:
   a substrate including a plurality of circuit elements;
   a metallization stack covering said substrate and configured and arranged to provide interconnections between the circuit elements;
   in the metallization stack, a top metallization layer having a plurality of metal portions embedded in an exposed porous material that laterally separates said plurality of metal portions, the porous material being configured and arranged to retain a liquid and to exhibit a dielectric constant that varies based upon an amount of the retained liquid; and
   a sensor circuit configured and arranged to provide an output indicative of the amount of the liquid retained in the porous material, based upon the dielectric constant.

2. The apparatus of claim 1, wherein
   the porous material is a patterned layer covering the plurality of metal portions, and
   the variation in the dielectric constant exhibited by the porous material is insensitive to water present in the atmosphere in a vapor or gas phase.

3. The apparatus of claim 1, wherein the sensor circuit manifests a selection of the circuit elements connected to the plurality of metal portions through the metallization stack, said selection being configured and arranged to provide the output by measuring the impedance between said metal portions.

4. The apparatus of claim 3, wherein neighboring metal portions of said plurality of metal portions that are separated by the porous material form a capacitor that is configured and arranged to provide the output based upon a capacitance set via the dielectric constant of the porous material between the neighboring metal portions.

5. The apparatus of claim 1, wherein the sensor circuit includes a plurality of terminals conductively coupled to respective ones of the metal portions of said plurality of metal portions, the terminals being configured and arranged to provide an indication of the impedance between said metal portions.

6. The apparatus of claim 1, wherein the porous material comprises a low-k dielectric material exhibiting water retention hysteresis behavior.

7. The apparatus of claim 6, wherein the low-k dielectric material comprises a plasma-treated carbon-doped silicon oxide.

8. The apparatus of claim 6, wherein the low-k dielectric material comprises SiLK.

9. The apparatus of claim 6, wherein the low-k dielectric material comprises nanoclustered silica.

10. The apparatus of claim 1, further comprising a capping layer covering the porous material, said capping layer comprising a plurality of capillaries for exposing the porous material.

11. The apparatus of claim 10, wherein the capping layer comprises an anodically oxidized aluminum.

12. An electronic device comprising the integrated circuit apparatus of claim 1.

13. The apparatus of claim 1, wherein the sensor circuit is configured and arranged to provide the output based upon ion conductivity between the metal portions.

14. The apparatus of claim 1, wherein the sensor circuit is integrated within the plurality of circuit elements.

15. The apparatus of claim 1, wherein the porous material includes a porous dielectric material and a porous capping layer, the dielectric material being configured and arranged to store water and the capping layer being configured and arranged to exhibit the dielectric constant that varies in response to an amount of water drawn into capillaries therein, from the porous dielectric material.

16. A method comprising:
    providing a substrate;
    forming a plurality of circuit elements on said substrate;
    forming a metallization stack covering said substrate for providing interconnections between the circuit elements;
    forming, on top of said metallization stack, a plurality of metal portions;
    embedding said plurality of metal portions in an exposed porous material for retaining a liquid, said porous material laterally separating said plurality of metal portions and configured to exhibit a dielectric constant that varies based upon an amount of the retained liquid, the variation in the dielectric constant exhibited by the porous material being insensitive to water present in the atmosphere in a vapor or gas phase; and
    forming a sensor circuit configured and arranged to provide an output indicative of the amount of the liquid retained in the porous material, based upon the dielectric constant.

17. The method of claim 16, further comprising patterning said porous material.

18. The method of claim 16, further comprising depositing a capping layer over said porous material, said capping layer comprising a plurality of capillaries for exposing the porous material.

19. The method of claim 16, wherein forming a sensor circuit includes forming a sensor circuit, in at least one of the circuit elements, coupled to respective ones of the metal portions for measuring the dielectric constant.

20. The method of claim 16, wherein forming a sensor circuit includes forming a capacitor including at least two of the metal portions separated by the porous material and configured and arranged to provide the output indicative of the amount of the liquid retained in the porous material by providing an output indicative of a capacitance between the metal portions.

* * * * *